United States Patent [19]
Pierpaoli et al.

[11] Patent Number: 6,054,428
[45] Date of Patent: Apr. 25, 2000

[54] EUTROPHIC DRUG COMPOSITIONS BASED ON TRANSFERRIN GLYCANS

[75] Inventors: Walter Pierpaoli, Ticino, Switzerland; Vladimir Lesnikov; Marina Lesnikova, both of Lake Forest Park, Wash.

[73] Assignee: Cellena AG, Ebmatingen, Switzerland

[21] Appl. No.: 09/208,593

[22] Filed: Dec. 10, 1998

Related U.S. Application Data

[63] Continuation of application No. PCT/EP97/03007, Jun. 10, 1997.

[30] Foreign Application Priority Data

Jun. 11, 1996 [EP] European Pat. Off. .............. 96401267

[51] Int. Cl.$^7$ ......................... A61K 31/715; A61K 38/13
[52] U.S. Cl. ............................... 514/11; 514/23; 514/42; 514/54
[58] Field of Search ...................... 536/1.11, 4.1, 536/17.2, 17.9, 18.2, 18.7, 22.1, 29.1, 123.1; 514/8, 9, 11, 12, 21, 23, 25, 42, 54

[56] References Cited

FOREIGN PATENT DOCUMENTS

| | | |
|---|---|---|
| 0 426 924 A1 | 5/1991 | European Pat. Off. . |
| 0 568 200 A2 | 11/1993 | European Pat. Off. . |
| 696455 | 2/1996 | European Pat. Off. . |
| 754459 | 1/1997 | European Pat. Off. . |
| WO 95/21618 | 8/1995 | WIPO . |
| WO 96/04930 | 2/1996 | WIPO . |

OTHER PUBLICATIONS

Genevieve Spik et al., "Comparative study of the primary structure of sero–, lacto–and ovotransferrin glycans from different species", Biochimie, vol. 70 (1988) pp. 1459–1469.

*Primary Examiner*—Jeffrey E. Russel
*Attorney, Agent, or Firm*—Birch, Stewart, Kolasch & Birch, LLP

[57] ABSTRACT

The use of transferrin glycans, particularly human transferrin glycans for the production of eutrophic drug compositions is disclosed. These transferrin glycans allow the toxic effects of cytotoxic drugs, e.g., cyclosporin, when used at high dosages or over prolonged times to be alleviated or even suppressed.

13 Claims, 1 Drawing Sheet

Protective effect of human pooled transferrins (Tf) and transferrin derived glycans (Gly) on aFas induced apoptosis of human bone marrow cells Results of five similar, repeated experiments
aFas – monoclonal antibodies – induced apoptosis Protective effect of human pooled transferrins (Tf) and transferrin derived glycans (Gly) on aFas induced apoptosis of human bone marrow cells Results of five similar, repeated experiments
aFas – monoclonal antibodies – induced apoptosis

EUTROPHIC DRUG COMPOSITIONS BASED ON TRANSFERRIN GLYCANS

This application is a continuation of PCT International Application No. PCT/EP97/03007 filed Jun. 10, 1997, which claims priority from European Patent Application No. 96401267.8 filed Jun. 11, 1996.

The invention relates to the production of new drugs, particularly eutrophic drugs, the active principle of which consists of transferrin glycans. The invention is of particular significance for human therapy. However it is not limited thereto. It may also be applicable in veterinary medicine.

BACKGROUND OF THE INVENTION

An eutrophic drug means a drug that is capable of maintaining or restoring the structure and function of organs, tissues and cells in a person's body, particularly when that person undergoes treatments with other drug principles which beyond the favorable specific clinical effects which they exert, are fraught with undesirable side effects and are thus liable of seriously injuring healthy cells of the body. Thus no matter how valuable the drug, difficulties may be encountered in monitoring its use in patients heavily in need for it. Such type of drugs shall hereinafter be referred to as "cytotoxic drugs".

An example of such cytotoxic drugs is the immunosuppressant cyclosporin which, as is well known, can also induce in the treated host muscular cramps accompanied by pain and/or nephrotoxicity that can ultimately produce severe renal dysfunction, as evidenced e.g., by falls in glomerular filtration rates.

Similarly, anti-inflammatory drugs can entail a full array of side effects ranging from gastric diseases to the general disturbance of the metabolism in the treated patient.

There is thus a strong need for a drug composition capable of overcoming some of the most important side effects of cytotoxic drugs, particularly to either prevent tissue degradation or promote the repair of damaged cells and tissue, more generally of assisting the natural principles which in the body participate to homeostasis.

SUMMARY OF THE INVENTION

International patent application no PCT/EP 95/03191 filed on Aug. 11 1995 discloses a eutrophic drug composition whose active principle consists of transferring. Reference may be made to that earlier International patent application for more details, relative to transferring.

It has now been discovered that the eutrophic activity of transferrins is in fact concentrated in their glycans.

Thus the present invention concerns more particularly a biological composition having eutrophic properties whose active principle consists of one or several transferrin-derived glycans, substantially free of transferrin polypeptide components (hereinafter "transferrin polypeptides") to which they are normally conjugated in transferrins.

DESCRIPTION OF THE PREFERRED EMBODIMENTS

Figure 1:
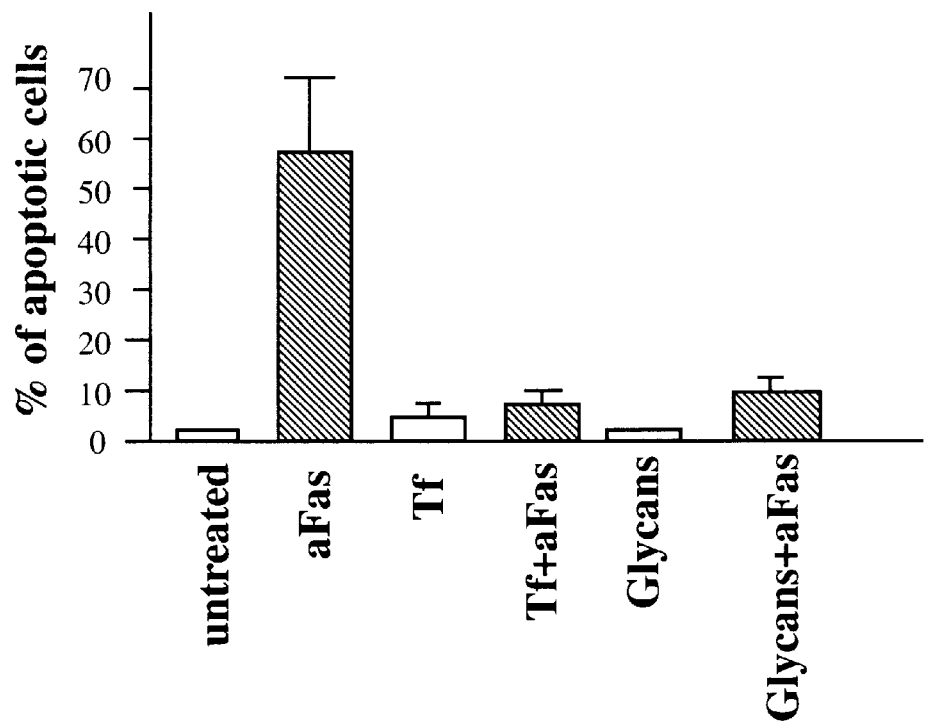
FIG. 1 illustrates on a comparative basis, the protective effects exerted on bone marrow cells by pooled transferring (Tf) and of transferrin derived glycans, substantially free of the transferrin-polypeptide components (Gly), against the effects of apoptotic agents, e.g., of apoptotic monoclonal antibodies designated as aFas.

Although not compulsory, the transferrin glycans should originate from the same mammal as the treated one. Thus human transferrin glycans should be the preferred active principle of eutrophic drugs for use in man.

The expression "transferrin glycans" as used throughout this patent disclosure further extends to all glycans which display a substantially similar profile as those directly obtained from transferrins, as evidenced by any of the analytical methods referred to in "Tools for Glycobiology" edited in 1994 by the Company known as Oxford GlycoSystems, available from the Company itself in the U.S.A., i.e., Oxford GlycoSystems, Inc., Cross Island Plaza, 133–33 Brookville Boulevard, Rosedale, N.Y. 11422, U.S.A., or from the European branch, i.e., Oxford Glyco-Systems Ltd., Hitching Court, Blacklands Way, Abingdon, OX14 1RG, UK.

Transferrin glycans as such have also been extensively studied: reference is made, of course in a non-limitative manner, to general publications describing them, for instance the publication titled "Comparative study of the primary structures of sero-, lacto- and ovotransferrin glycans from different species" of Geneviève Spik et al., in Biochimie 70 (1988) 1459–1469, which describes transferrin glycans obtained from various mammalian species.

As glycoproteins, all transferrins of human and animal origin contain carbohydrates in amounts varying from 2 to 12%. Human serum transferrin has been found to present a microheterogeneity based on the existence of bi- and triantennary glycans of the N-acetyl-lactosaminic type. Three carbohydrate molecular variants of transferrins could be distinguished: Tf-I (less than 1%) containing two triantennary glycans, Tf-II (approx. 17%) with one triantennary and one biantennary glycan and Tf-III (approx. 82%) containing two biantennary glycans. The relative proportions of these variants were found to change in women in the last trimester of pregnancy, the variants I and II showing an increase in contrast to variant III, which was found to decrease to approx. 67% (see Leger et al. referred to hereafter). In addition, it has been established, that human sero-transferrin contains two asparagine glycosylation sites in the C-terminal part of its single polypeptide chain and that the glycans are fully sialytated and not fucosylated. Like the corresponding transferrins, the glycans which can be obtained therefrom display similar microheterogeneities.

Detection of the mammalian species from which particular transferrin glycans originate can be carried out by any person skilled in the art, e.g., by reaction of these glycans with sets of antibodies previously obtained against glycans of a number of different mammalian species, among which presumably that of the species from which the glycans under study may originate. By way of non-limitative illustration, recourse can be had to a method of the type disclosed in the publication titled "Physiological significance of the marked increased branching of the glycans of human serotransferrin during pregnancy" of Didier Léger et al. in Biochem. J., 257: 231–238 (1989) (Printed in Great Britain).

For instance transferrin glycans obtained from a human may be detected by an immunological reaction with antibodies specific to human glycans—or even to the corresponding human transferrins and then with horse-radish-peroxidase—conjugated second antibodies raised against tIg6, in accordance with Towbin et al. (1979) Proc. Natl. Acad. Sci. U.S.A. 79: 1175–1179 and Burnette et al. (1981) Anal. Biochem. 112: 195–203.

Of course other types of reactions can be envisaged for the same purpose, e.g., by comparative analysis of the electrophoretic behavior of the glycans under study and standards obtained from transferrins themselves obtained from different mammalian species.

Particularly transferrin glycans for use in the eutrophic compositions according to the invention can be obtained from the corresponding transferrins by any of the well known methods applicable to the removal of the polypeptides and recovery of the corresponding glycans, e.g., a method of hydrazinolysis such as disclosed in the publication of S. Takasaki et al. titled "Hydrazinolysis of Asparagine-Linked Sugar Chains to Produce Free Oligosaccharides" in "Methods of Enzymology" (1982) Vol. 83: 263–268, or in the publication of T. Patel et al., titled "Use of Hydrazine to Release in Intact and Unreduced Form both N- and O-Linked Oligosaccharides from Glycoproteins" in Biochemistry (1993) 32:679–693; or by enzymatic cleavage in the presence of a neuraminidase or an endoglycosidase activity, such as that produced by *Flavobacterium meningosepticum*, as disclosed by J. H. Elder et al. (1982) in the publication titled "Endo-β-N-Acetylglucosaminidase F: Endoglycosidase from *Flavobacterium meningosepticum* that cleaves both high-mannose and complex glycoproteins" in Proc. Natl. Acad. Sci. U.S.A., Vol. 79:4540–4544, August 1982, or in the presence of the endo-β-N-acetylglucosaminidase F (Endo F) or peptide: N-glycosidase F (PNGase F) also obtainable from cultures of *Flavobacterium meningosepticum* as disclosed by A. L. Tarentino et al. in the publication titled "Deglycosylation of Asparagine-Linked Glycans by Peptide:N-Glycosidase F".

Reference can also be made to the techniques generally disclosed in "Tools for glycobiology" supra.

Advantageously, transferrin glycans are obtained from pooled transferrins themselves obtained from human plasma pools produced in the industry of blood products. Such plasma pools often originate from several hundreds to several thousands of donors. Advantageously, these transferrins result from the purification product obtained from blood of at least 1000 donors.

Pooled transferrin-derived glycans of human origin can be obtained from transferrins which are themselves available in the trade: see "Tools for Glycobiology" already of record. Human transferrin-derived glycans, substantially free of the transferrin polypeptides are available, e.g., at Oxford Glyco Systems, Inc. Thus transferrin glycan pools are readily accessible.

Though it is unlikely that the genetic diversity of transferrins of different sources is liable of influencing significantly their eutrophic properties, the use of pools of transferrin glycans would remove that influence, if indeed any.

Though no relationship has so far really been established between the genetic diversity of transferrins and the major histocompatibility complex (MHC) system in man, the serological detection and confirmation of the presence of a sufficient number of the dominant and relevant HLA can nonetheless be relied upon to verify whether plasma pools from which the corresponding pooled transferrins are to be obtained originated from a sufficient number of donors. For instance a preferred starting plasma pool should prove to contain at least 4 serologically determinable antigens of each of the so-called HLA-A, HLA-B, HLA-C, HLA-D and HLA-DR series. Reference is for instance made to FIG. 31, page 70 of the book titled "Medical Immunology" edited in 1979 by James Irvine, Teviot Scientific Publications, Ediburgh, Great Britain.

The invention finds particularly advantageous uses in the protection of persons subjected to an immunosuppressive treatment, particularly with cyclosporin or other immunosuppressive drugs, e.g., FK506 or rapamycin. As a matter of fact, transferrin glycans have been found to efficiently counteract the toxic effects of such drugs, as this can be verified upon observing the homeostatic or eutrophic effect of transferrin glycans on different metabolic functions in animals subject to treatments with cyclosporin, when they are either prolonged or carried out with high dosages.

The eutrophic activities have been assayed upon resorting, e.g., to those tests which have already been disclosed in International patent application no PCT/EP 95/03191 already made of record hereabove.

Particularly, the effects can be observed at the histological level. As is well known, the organs which are susceptible to the toxic side effects of chronic administration of cyclosporin are particularly the kidneys.

Transferrin glycans are of particular interest in association with cyclosporin or other drugs having similar immunosuppressive effects.

The transferrin glycans can also be used to combat toxic effects of other cytotoxic agents or compounds, particularly of those known to induce kidney damage to be substantially diminished, let alone eliminated. By way of example of such other drugs, one may mention:

antibiotics, particularly Polyene antibiotics, such as Colimycin and Gentamycin;

non-steroid anti-inflammatory drugs, particularly Ibuprofen;

anti-tumor drugs, such as Cis-platinum, or other immunosuppressive and cytotoxic drugs like prednisolone or cyclophosphamide;

antiviral drugs or mixtures of drugs, such as those recommended for the treatment of AIDS.

As already mentioned, the invention is not restricted to the use of transferrin glycans in association with drugs which target principally the kidneys. Transferrin glycans can also be used to prevent the damage of other tissues, for instance for the sake of preventing ear damages produced in a number of patients by Gentamycin, Cis-platinum or streptomycin, by way of examples.

The compositions of the invention are further not limited to the use of transferrin glycans in association with a cytotoxic drug. Their use can be extended to other forms of therapy, e.g., radiotherapy in the case of cancer. Their use is all the more beneficial as particularly natural transferrin glycans are devoid of toxicity.

Whatever the nature of the cytotoxic therapeutical compound or agent used, it will be appreciated that transferrin glycans will then enable limitations in dosage or in duration of the treatments to be overcome, thereby providing for a beneficial effect of the "cytotoxic drug" administered, with a concomitant reduction, let alone suppression of the mentioned side effects.

The amounts of the transferrin glycans to be administered will vary to a considerable extent depending upon the nature of the cytotoxic drug with which it is to be associated. Simply for the purpose of giving non-limitative examples, daily administrations of transferrin glycans in a human should range normally from 2 mg to 10 mg/kg of body weight, particularly when injected intravenously, or from 5 mg to 50 mg/kg of body weight when injected intramuscularly. Obviously, the dosages should be left with the clinician. They may also vary according to the dosages of the cytotoxic drugs which are selected by the clinician.

Generally speaking the invention further relates to compositions containing both the transferrin glycans and the cytotoxic drug. It will readily appear to the person skilled in the art that two principles may be administered either in admixture or sequentially at alternate times.

Thus the invention concerns more particularly:

the use of transferrin glycans, preferably human transferrin glycans, substantially free of transferrin polypeptide components, for the production of drug compositions effective to reduce, let alone suppress the cytotoxic side effects of a therapeutically active agent or compound, e.g., an immuno-suppressive drug, such as cyclosporin, displaying cytotoxic effects, when administered in association therewith to a host undergoing a treatment with said therapeutically active agent, the use of said transferrin glycans for the production of drug compositions, in which said transferrin glycans are in admixture with said therapeutically active agent or compound, in amounts effective to reduce, let alone eliminate the cytotoxic side effects of said therapeutically active agent or compound, the use of said transferrin glycans for the production of eutrophic drug compositions containing said transferrin glycans in amounts effective to reduce, let alone eliminate side effects of a therapeutical treatment, such as irradiation, when said eutrophic drug composition is administered concurrently with said therapeutical treatment, and finally therapeutical compositions containing one or several therapeutically active principles which however have cytotoxic activity, in association with transferrin glycans, advantageously human pooled transferrin glycans, substantially free of transferrin polypeptide components, said transferrin glycans being in amounts relative to the therapeutically active principle effective to alleviate the cytotoxic side effects of the latter when administered to a host, particularly a human patient.

The experimental data which follow provide for a further illustration of the beneficial properties of the transferrin glycans which properties provide an additional basis for their prospective value as active principles for use in the production of eutrophic drug compositions, particularly for use in the different applications which have been disclosed herein and which are further referred to in the claims.

Anti-Apoptotic Action of Human Pooled Transferrins (Tf) and Transferrin Derived Glycans (Gly) (Short-Term Bone Marrow Culture Model)

Mononuclear cells of the bone marrow were separated by Ficoll-Hypaque density gradient, washed twice with Waymouth medium and resuspended in Human Dexter medium (10% FCS) to a final concentration $1-2 \times 10^6$ cells/ml.

The cells were distributed in 24-wells plates, 1 ml each.

Preliminary work (10 experiments) was performed to work out the optimal conditions for this study: cell concentrations, Tf and Gly doses, the time of cell exposure to the substances under study, apoptosis inducing agent. On the basis of these preliminary experiments, five similar repeated experiments were carried out, and the summary of these 5 experiments is presented as results.

aFas as apoptosis inducing agent was added at a dose of 100 ng/ml, 15 hrs before harvesting.

Human pool transferrin (Tf) (5 µg/ml) or Glycans (Gly) (0.25 µg/ml) were added 40 hrs before harvesting.

The samples were as following:

1. Untreated BMC
2. aFas
3. Tf
4. Tf+aFas
5. Gly
6. Gly+aFas

Cell Cycle Analysis

Flow cytometry is a well-established procedure for analysis of surface antigens. By using simple, reliable methods for staining nuclear DNA, cell cycle compartment analysis can be used to measure lymphocyte activation and proliferation, and apoptosis (programmed cell death). Cells in suspension are fixed with ethanol and stained with propidium iodide (PI). PI intercalates into double-stranded nucleic acids and can be excited by 488-nm laser used in commonly available flow cytometers. The enzyme Rnase A is used to degrade double-stranded RNA so that only double-stranded DNA is left within the cell to bind PI. Upon binding to DNA, PI fluorescence increases ~50-fold, improving signal-to-noise ratios, and is sufficiently bright to be used with low power air-cooled lasers. The red emission of PI centers around 600 nm and can be readily discriminated in commercial cytometers from FITC immunoflourescence emission centered at ~510 nm.

Becton Dickinson FACScan was used.

It was found that Tf and Gly are involved in the regulation of apoptosis. aFas induced apoptosis in normal human bone marrow cells at a level of ~58% after 15 hrs treatment. Preincubation of these cells either with Tf alone or with Gly alone decreased significantly the level of apoptosis in the cells, caused by the addition of aFas. Results of five similar repeated experiments (Means±SE) are shown in FIG. 1.

Eutrophic Effect of Transferrin-Derived Glycans

30 BALB/c 4 month-old female mice were used to investigate the protective (eutrophic) effect of human pooled transferrin (Tf) and transferrin-derived glycans (Gly) in repeatedly immunosuppressed animals.

Initial immunosuppression (IS) of the mice with prednisolone (Pr) and cyclophosphamide (Cy) combination on day 0, 1 was followed by additional Cy injection on day 31 and on day 42 of the experiment.

IS mice were injected with Tf (200 ug/mouse i.p. in 0.5 ml—Group 2) or with Gly (5 ug/mouse i.p. in 0.5 ml—Group 3) on day 2, 3, 4 and 5 of the experiment, control animals (Group 1) received 0.5 ml saline on the same days of the experiment.

Some improvements of blood parameters were observed on day 15 of the experiment in mice which had received Tf or Gly versus control group. On day 68, the survival rate in Tf treated mice was 60%, in Gly treated mice —50%, and in control mice—40%. Blood leukocyte number and percentage of lymphocytes were considerably higher than these parameters in control mice (Table 1).

20 CD-1 (outbred) 2 month-old female mice were used to investigate the protective effect of Tf and Gly in cyclosporine treated animals.

The mice were divided into four groups, 5 mice each. The mice of Groups 2–4 were injected with 30 mg/kg cyclosporine (CsP) subcutaneously (s.c.) in 0.2 ml every other day for one month, and with 10 mg/kg Tf intraperitoneally (i.p.) in 0.5 ml (Group 3), or with 0.17 mg/kg Gly i.p. in 0.5 ml (Group 4), or with 0.5 ml saline i.p. (Group 2). The mice of additional control group were injected with 0.2 ml saline s.c. and with 0.5 ml saline i.p. (Group 1) every other day for one month.

One month after the beginning of the experiment the mice were sacrificed and blood parameters were measured.

A strong tendency to increased blood leukocyte number and percentage of blood lymphocytes was found in CsP treated mice which had received Tf or Gly in comparison with these parameters of CsP treated mice which had received saline (Table 2).

TABLE 1

IMMUNOPROTECTIVE EFFECT OF HUMAN POOL TRANSFERRINS (Tf) AND TRANSFERRIN-DERIVED GLYCANS (Gly) IN CHEMICALLY IMMUNOSUPPRESSED MICE

| groups | day 15 | | | day 68 | | | |
|---|---|---|---|---|---|---|---|
| | $\Delta$ BW | Leukocytes x $10^6$ cells/ml | % Lymphocytes | $\Delta$BW | TW/BW | Leukocytes x $10^6$ cells/ml | % Lymphocytes |
| Gr. 1 saline | $-4.5$ g (n = 9) | $2.6 \pm 0.7$ (n = 3) | $11 \pm 2.7$ (n = 3) | $-7.1$ g (n = 4) | $0.6 \pm 0.1$ (n = 4) | $3.6 \pm 0.6$ (n = 4) | $23 \pm 6.2$ (n = 4) |
| Gr. 2 Tf pool | $-5.7$ g (n = 8) | $4.6 \pm 1.1$ (n = 3) | $18 \pm 3.1$ (n = 3) | $-4.4$ g (n = 6) | $0.72 \pm 0.1$ (n = 6) | $5.9 \pm 0.6$* (n = 6) | $50 \pm 4.3$* (n = 6) |
| Gr. 3 Gly | $-5.6$ g (n = 5) | $4.8 \pm 0.8$ (n = 3) | $34 \pm 6.1$ (n = 3) | $-4.9$ g (n = 5) | $0.85 \pm 0.2$ (n = 5) | $5.2 \pm 0.5$* (n = 5) | $52 \pm 7.3$** (n = 5) |

*$p < 0.05$ vs Gr. 1; **$p < 0.02$ Gr. 1
$\Delta$ BW - loss of body weigt; TW/BW - Thymus/body weight ratio; IS - immunosuppression; IS: Prednisolon - 100 mg/kg intraperitoneally (i.p.) on day 0; Cyclophosphamide - 200 mg/kg i.p. on day 0, 1, 31, 42; Group 1 (n = 10) IS + saline i.p. on day 2–5
Group 2 (n = 10) IS + Tf human pool 200 μg/mouse on day 2–5
Group 3 (n = 10) IS + Gly 5 μg/mouse i.p. on day 2–5

TABLE 2

BLOOD PARAMETERS IN CYCLOSPORINE (CsP) TREATED MICE RECEIVING HUMAN POOL TRANSFERRINS (Tf), TRANSFERRIN-DERIVED GLYCANS (Gly) OR SALINE
(1 month after the beginning of the experiment: 5 mice for each group)

| groups | Leukocytes x $10^6$ cells/ml | % lymphocytes | Absolute lymphocyte number x $10^6$ cells/ml |
|---|---|---|---|
| Gr. 1 (sal + sal) | $5.3 \pm 0.4$ | $80.8 \pm 2.3$ | $4.4 \pm 0.4$ |
| Gr. 2 (CsP + sal) | $2.4 \pm 0.7$ | $67.2 \pm 3.3$ | $1.4 \pm 0.6$ |
| Gr. 3 (CsP + Tf) | $3.0 \pm 0.7$ | $73.8 \pm 3.2$ | $2.2 \pm 0.4$ |
| Gr. 4 (CsP + Gly) | $3.6 \pm 0.7$ | $72.6 \pm 1.0$ | $2.6 \pm 0.5$ |

Gr. 1 - 0.2 ml saline, subcutaneously (s.c.) + 0.5 ml saline i.p., every other day for 1 month.
Gr. 2 - 30 mg/kg CsP s.c. in 0.2 ml + 0.5 ml saline i.p., every other day for 1 month.
Gr. 3 - 30 mg/kg CsP s.c. in 0.2 ml + 10 mg/kg Tf i.p. in 0.5 ml, every other day during 1 month.
Gr. 4 - 30 mg/kg CsP s.c. in 0.2 ml + 0.17 mg/kg Gly i.p. in 0.5 ml, every other day for 1 month.

What is claimed is:

1. A therapeutic composition which comprises:
   a) at least one therapeutically active compound which has cytotoxic activity;
   b) at least one transferrin glycan in an amount effective to alleviate the cytotoxic side effects of said therapeutically active compound when administered to a host, wherein said composition is substantially free of transferrin polypeptide components.

2. The therapeutic composition according to claim 1, wherein said transferrin glycans are human pooled transferrin glycans.

3. The therapeutic composition according to claim 1, wherein said therapeutically active compound is an immunosuppressive drug.

4. The therapeutic composition according to claim 3, wherein said immunosuppressive drug is cyclosporin.

5. A method for reducing the cytotoxic side effects of a therapeutically active compound which comprises administering, to a host undergoing treatment with said therapeutically active compound, at least one transferrin glycan, substantially free of transferrin polypeptide components, in an amount sufficient to reduce said cytotoxic side effects.

6. The method according to claim 5, wherein said transferrin glycans are pooled transferrin glycans.

7. The method according to claim 5, wherein said transferrin glycans are of human origin.

8. The method according to claim 6, wherein said transferrin glycans are of human origin.

9. The method according to claim 5, wherein said therapeutically active compound is an immunosuppressive drug.

10. The method according to claim 8, wherein said therapeutically active compound is an immunosuppressive drug.

11. The method according to claim 9, wherein said immunosuppressive drug is cyclosporin.

12. The method according to claim 10, wherein said immunosuppressive drug is cyclosporin.

13. The method according to any one of claims 5–12, wherein said transferrin glycans and said therapeutically active compound are administered in admixture.

* * * * *